(12) United States Patent
Coveney

(10) Patent No.: US 9,663,507 B1
(45) Date of Patent: May 30, 2017

(54) CRYSTALLISATION OF THIAMINE HYDROCHLORIDE

(71) Applicant: Topchem Pharmaceuticals Limited, County Sligo (IE)

(72) Inventor: Donal Coveney, Sligo (IE)

(73) Assignee: Topchem Pharmaceuticals Limited (IE)

( * ) Notice: Subject to any disclaimer, the term of this patent is extended or adjusted under 35 U.S.C. 154(b) by 0 days.

(21) Appl. No.: 15/264,042

(22) Filed: Sep. 13, 2016

(51) Int. Cl.
*C07D 417/06* (2006.01)

(52) U.S. Cl.
CPC ........ *C07D 417/06* (2013.01); *C07B 2200/13* (2013.01)

(58) Field of Classification Search
CPC ...................................................... A61K 9/14
See application file for complete search history.

(56) References Cited

U.S. PATENT DOCUMENTS 5,290,568 A * 3/1994 Asogawa ............. C07D 415/00
424/489

OTHER PUBLICATIONS

Ruth L. Te, et al X-ray Diffractionand Solid-State NMR Investigation of the Single-Crystal to Single-Crystal Dehydration of Thiaminie Hydrochloride Monohydrate, Crystal Growth & Design 2003, vol. 3. No. 6, 997-1004.
Paroma Chakravarty, et al., Characterization and Structure Analysisof Thiamine Hydrochloride Methanol Solvate, Crystal Growth & Design 2010, vol. 10, 4414-4420.
Atsushi Watanabe, et al., Polymorphism of Thiamine hydrochloride, Crystal Structure of Thiamine hydrochloride Hemihydrate and Its Stability, Chem, Pharm Bull. 27(11) 2751-2759(1979).
Katsuhiko Masuda, et al., Study of the Pseudo-Crystalline Transformaton from Form I to Form II of thiamine Hydrochloride (Vitamin B) Chem. Pharm. Bull 59(1) 57-62 (2011).

* cited by examiner

*Primary Examiner* — Paul V Ward
(74) *Attorney, Agent, or Firm* — Caesar Rivise, PC

(57) ABSTRACT

A method of producing crystalline pharmaceutical grade Thiamine hydrochloride by crystallization from an isopropanol-water mixture. The method can be tuned to produce either the hemihydrate or monohydrate forms in a simple and easy manner.

10 Claims, 1 Drawing Sheet

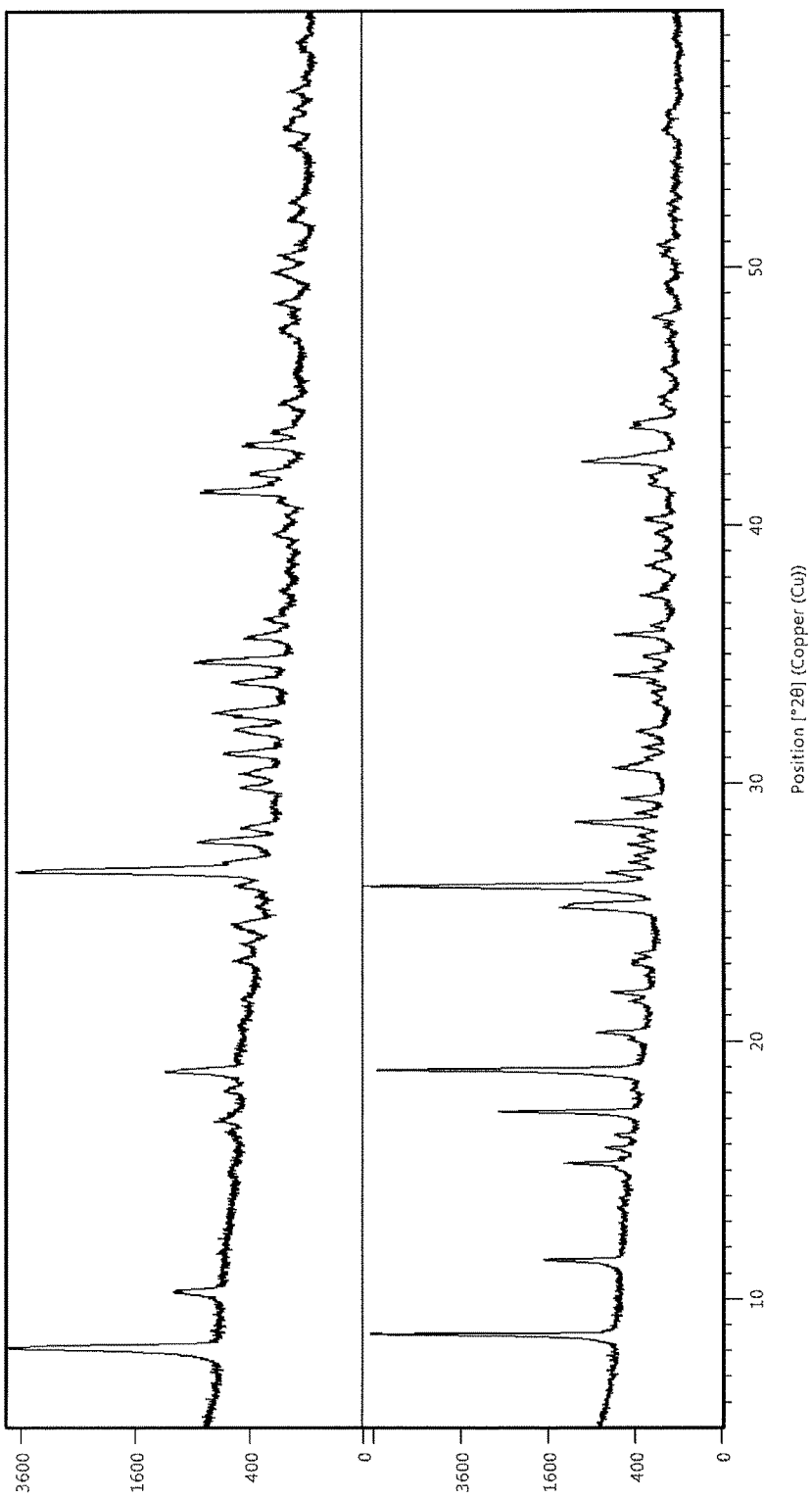
Fig 1 A powder X-ray diffraction pattern (CuKα, 40kV, 35mA) for Thiamine hydrochloride hemihydrate crystallised from isopropanol water.
Fig. 2 A powder X-ray diffraction pattern (CuKα, 40kV, 35mA) for Thiamine hydrochloride monohydrate crystallised from isopropanol water.

CRYSTALLISATION OF THIAMINE HYDROCHLORIDE

FIELD OF THE INVENTION

The invention relates to a method of producing pharmaceutical grade Thiamine hydrochloride hydrates.

BACKGROUND OF THE INVENTION

Thiamine hydrochloride is administered in both injectable and solid oral dosage pharmaceutical preparations either singly or in combination with other vitamins and minerals.

Commercially available grades of Thiamine hydrochloride are generally food grade and not necessarily suitable for pharmaceutical use. The increasing regulatory oversight by international agencies such as the United States Food & Drug Administration places restrictions on manufacturers of pharmaceutical preparations.

Ready access to pharmaceutical grade Thiamine hydrochloride meeting current pharmaceutical regulatory standards is therefore highly desirable.

OBJECTS OF THE INVENTION

Thiamine hydrochloride is known to exist in a number of crystalline forms: a monohydrate, hemihydrate, anhydrous and a methanol solvate. These four crystalline forms are readily distinguished from each other by powder X-ray diffraction.

The monohydrate is the commonest from and is generally found in commercial material. This monohydrate has been described as a nonstoichiometric hydrate with approximately one mole of water present (Ref 1: P. Chakravarty & R. Suryanarayanan. Crystal Growth & Design, 10, 4414 (2010)). This monohydrate loses water easily to form the anhydrous form. The monohydrate is also referred to as Form 1 or the α Form. The monohydrate is hygroscopic and it has been shown that on exposure to humidity the monohydrate initially absorbs water and then converts to the hemihydrate with loss of water (Ref 2: K. Masuda et al, Chem. Pharm. Bull., 59,57 (2011)). This conversion occurs with both the pure substance and in tablets but the conversion occurs more readily in the pure substance (Ref 2).

The hemihydrate on the other hand does not lose water easily and must be heated to high temperature in order to convert to the anhydrous form. The hemihydrate is less hygroscopic and is more stable than the monohydrate. For this reason the hemihydrate is considered to be more suited to use in pharmaceutical formulations, particularly in tablet form. The hemihydrate is also referred to as Form 2 or the β Form.

The anhydrous form is most easily prepared by dehydration of the monohydrate. The anhydrous form readily absorbs moisture to form the monohydrate and hemihydrate. This anhydrous form is therefore not useful for pharmaceutical formulations.

The methanol solvate desolvates readily to the anhydrous form even on gentle heating and on exposure to humidity converts to the monohydrate and hemihydrate (Ref. 1). This methanol solvate therefore has no practical utility in a pharmaceutical formulation.

U.S. Pat. No. 5,290,568 discloses a process where the monohydrate can be converted to the hemihydrate on a commercial scale by heating the monohydrate in a fluidised bed granulator or kneader. Seeding with the hemihydrate is required; otherwise the conversion does not occur to any substantial degree. This invention claims greater stability of the hemihydrate towards heat and moisture and as such is more suited to tabletting.

Crystallisation is generally accepted as the most versatile method of purification of pharmaceutical substances and is applicable across a wide range of scales in conventional, readily available equipment.

Crystallisation of thiamine hydrochloride has been reported from aqueous methanol and aqueous ethanol. The monohydrate is readily formed in these crystallisations. For example (Ref.3: Crystal Growth & Design, Vol. 3, No. 6, 997 (2003), crystallisation from 70-80% ethanol produced the monohydrate.

The hemihydrate is more difficult to access by crystallisation. For example (Ref. 4: Chem. Pharm. Bull. 27 (11), 2751 (1979)) teaches how the hemihydrate can be obtained by crystallisation from water by seeding with the hemihydrate. The yield is not reported but given the high solubility in water of Thiamine hydrochloride, this is not a suitable commercial process.

Thiamine hydrochloride is widely available as food grade quality and generally as the monohydrate. A simple crystallisation method to upgrade thiamine hydrochloride to pharmaceutical grade is therefore highly desirable. Control over the level of hydration is also necessary to ensure reliability and robustness in the method.

BRIEF DESCRIPTION OF THE DRAWINGS

FIG. 1 A powder X-ray diffraction pattern (CuKα, 40 kV, 35 mA) for Thiamine hydrochloride hemihydrate crystallised from isopropanol water.

FIG. 2 A powder X-ray diffraction pattern (CuKα, 40 kV, 35 mA) for Thiamine hydrochloride monohydrate crystallised from isopropanol water.

SUMMARY OF THE INVENTION

The present inventor made intensive investigations to solve the above problem and developed a robust crystallisation method to produce pharmaceutical grade Thiamine hydrochloride. The inventor unexpectedly found that careful tuning of the said crystallisation from aqueous isopropanol can selectively produce either monohydrate or hemihydrate crystals of Thiamine hydrochloride in pure form.

Further investigations of these findings have now led to the completion of the present invention.

The invention thus provides:
  (1) A method of producing pharmaceutical grade crystalline Thiamine hydrochloride via crystallisation from an isopropanol water mixture.
  (2) A method as described under (1) above where the volume of water used is in the range of 0.7 to 1.5 liters per kilogram of the input of Thiamine hydrochloride.
  (3) A method as described under (1) above where the volume of isopropanol used is in the range of 2 to 20 liters per kilogram of the input of Thiamine hydrochloride.
  (4) A method as described under (1) above where the monohydrate of Thiamine hydrochloride is selectively produced when the mechanical agitation speed of the crystallisation mixture is set below 150 rpm and preferably at 125 rpm.
  (5) A method as described under (1) above where the hemihydrate of Thiamine hydrochloride is selectively produced when the mechanical agitation speed of the crystallisation mixture is set above 180 rpm and preferably at 200 rpm.

DETAILED DESCRIPTION OF THE INVENTION

The crystallisation of thiamine hydrochloride was studied using food grade thiamine hydrochloride monohydrate as starting material. A mixture of isopropanol and water was found to be an excellent crystallisation medium. Thiamine hydrochloride is dissolved in USP grade water and this solution is filtered to remove any particulates.

Mixing this solution with pre-filtered isopropanol results in crystallisation. Filtration, washing with fresh isopropanol and vacuum drying leads to pharmaceutical grade thiamine hydrochloride.

The volume of water used is in the range of 0.7 to 1.5 liters per kilogram of the input of Thiamine hydrochloride. A certain minimum volume of water is required to fully dissolve the input material and excess water leads to poor yields. The preferred amount of water is 0.8 liters per kilogramme of Thiamine hydrochloride.

The volume of isopropanol used is in the range of 2 to 20 liters per kilogram of the input of Thiamine hydrochloride. A certain minimum volume of isopropanol is required to obtain acceptable economic recovery. Increasing the excess beyond the recommended range is not detrimental but does not improve recovery. The preferred amount of Isopropanol is 4 liters per kilogramme of Thiamine hydrochloride.

When studying the crystallisation at kilo-scale it was discovered that varying the speed of the mechanical agitation resulted in a surprising selectivity of either monohydrate or hemihydrate forms. No seeding is required. Simply agitating at lower speeds during the crystallisation leads to the monohydrate in pure form. Increasing the agitation speed unexpectedly leads to the hemihydrate in pure form.

Specifically agitation at speeds below 150 rpm leads to the monohydrate exclusively. Conversely by agitation above 180 rpm, the hemihydrate is formed exclusively. The integrity of each form is confirmed by powder X-ray diffraction. It has been well established in the literature that the monohydrate and hemihydrate are easily distinguished from each other by powder X-ray diffraction (e.g. Ref. 1). The hemihydrate characteristic peaks are at 8.1 and 10.3 2θ while the monohydrate characteristic peaks are at 8.5 and 11.4 2θ.

As can be seen in FIG. 1 and FIG. 2, the hemihydrate and monohydrate forms generated by this invention demonstrate distinctly different patterns. The characteristic peaks at 8.1 and 10.3 2θ in FIG. 1 match the hemihydrate while the monohydrate characteristic peaks are at 8.5 and 11.4 2θ are clearly visible in FIG. 2. It is also clear that each form is substantially free of the other form.

Intermediate agitation speeds may lead to one or the other hydrate and this is not well controlled by attempted seeding with the desired hydrated form.

Similarly if the monohydrate form is agitated rapidly in the crystallisation mixture, the material converts to the hemihydrate form.

The hemihydrate form has been reported as more stable than the monohydrate and as such the hemihydrate is more suited to oral dosage forms. However, the thiamine hydrochloride monohydrate produced by this invention demonstrates remarkable stability when protected from moisture and stored in thermally sealed foil lined polypropylene bags. Testing according to the United States Pharmacopeia or European Pharmacopeia demonstrates stability up to three years as outlined in Table 1.

TABLE 1

3 Year Stability data of Thiamine hydrochloride monohydrate

| | Lot Number: | T111116 | | T111201 | | T111202 | |
|---|---|---|---|---|---|---|---|
| RESULTS | Limit | Time 0 | 36 Months | Time 0 | 36 Months | Time 0 | 36 Months |
| Appearance | Meets EP 8.6 | Complies | Complies | Complies | Complies | Complies | Complies |
| ID: FTIR | Meets USP 39 | Complies | Complies | Complies | Complies | Complies | Complies |
| ID: Chloride | Meets USP 39 | Complies | Complies | Complies | Complies | Complies | Complies |
| pH | Meets USP 39 (pH 2.7-3.4) | pH 3.3 | pH 2.9 | pH 3.2 | pH 3.0 | pH 3.2 | pH 3.1 |
| Water | Meets USP 39 (NMT* 5.0%) | 3.2% | 3.7% | 2.0% | 2.7% | 3.3% | 4.0% |
| Residue on Ignition | Meets USP 39 (NMT 0.2%) | 0.0% | 0.0% | 0.0% | 0.0% | 0.0% | 0.0% |
| Absorbance of Solution | Meets USP 39 (NMT 0.025 Abs) | 0.005 Abs | 0.004 Abs | 0.008 Abs | 0.013 Abs | 0.007% | 0.007 Abs |
| Limit of Nitrate | Meets USP 39 | Complies | Complies | Complies | Complies | Complies | Complies |
| Assay | 98.0%-102.0% | 99.0% | 99.8% | 98.6% | 99.6% | 99.2% | 99.1% |
| Solution S | Meets EP 8.6 (Practically Clear and Odorless) | Complies | Complies | Complies | Complies | Complies | Complies |
| Heavy Metals | Meets EP 8.6 | Complies | Complies | Complies | Complies | Complies | Complies |
| Sulfates | Meets EP 8.6 (NMT 300 ppm) | Complies | Complies | Complies | Complies | Complies | Complies |
| Related. Substances | EP 8.6 HPLC Method | | | | | | |
| Thiamine sulfate ester (Impurity A) | NMT 0.15% | <0.05% | 0.07% | 0.07% | 0.07% | 0.06% | 0.07% |
| Desmethylthiamine (Impurity B) | NMT 0.3% | <0.05% | 0.07% | 0.07% | 0.07% | 0.06% | 0.06% |
| Chlorothiamine (Impurity C) | NMT 0.15% | <0.05% | <0.05% | <0.05% | <0.05% | <0.05% | <0.05% |
| Unknown Impurities | NMT 0.10% | ND† | ND† | ND† | ND† | ND† | ND† |
| Total Impurities | NMT 0.5% | Complies | 0.13% | 0.4% | 0.14% | 0.12% | 0.13% |

*ND = Not Detected
†NMT = Not More Than

The present invention offers a simple scalable method to produce pharmaceutical grade thiamine hydrochloride in either monohydrate or hemihydrate forms in a controlled manner.

While the present invention has been described in terms of its specific embodiments, certain modifications and equivalents will be apparent to those skilled in the art and are intended to be included within the scope of the present invention.

The following examples are further illustrative of the present invention.

Example 1—Preparation of Thiamine Hydrochloride Hemihydrate

Thiamine hydrochloride (3.3 kg) is dissolved in 2.64 liters of USP Purified water by heating to 70° C. The resulting hot solution is filtered through a 15-40 micron in-line filter into a 20 liter vessel fitted with an anchor agitator and internal temperature monitor. The agitator is set at 220 rpm. Isopropanol (13.2 liters) is filtered through a 1 micron in-line filter and added slowly added to the agitated aqueous solution of thiamine hydrochloride while maintaining the temperature at 70° C. The resulting slurry is then cooled to 20° C. The crystalline thiamine hydrochloride is filtered and the filter cake is washed with isopropanol. The crystals are dried under vacuum at 50° C. to yield 2.84 kg of thiamine hydrochloride hemihydrate as confirmed by powder x-ray diffraction (FIG. 1).

Example 2—Preparation of Thiamine Hydrochloride Monohydrate

Using the conditions outlined in Example 1 but with an agitation speed of 125 rpm, the monohydrate of thiamine hydrochloride is prepared as confirmed by powder x-ray diffraction (FIG. 2).

Example 3—Preparation of Thiamine Hydrochloride Monohydrate

Using the conditions outlined in Example 2 but with the addition of the aqueous thiamine hydrochloride solution to isopropanol, thiamine hydrochloride monohydrate is prepared.

I claim:

1. A method of producing pharmaceutical grade crystalline Thiamine hydrochloride without the use of a seed crystal comprising the steps of:
   (a) dissolving Thiamine hydrochloride in water to form an aqueous Thiamine hydrochloride solution;
   (b) mixing the aqueous Thiamine hydrochloride solution with isopropanol while agitating the mixture;
   (c) crystallizing the mixture to produce crystalline Thiamine hydrochloride.

2. A method as described in claim 1, wherein the crystalline Thiamine hydrochloride comprises either Thiamine hydrochloride monohydrate or Thiamine hydrochloride hemihydrate.

3. A method as described in claim 1, wherein the volume of water used is in the range of 0.7 to 1.5 liters per kilo of input of Thiamine hydrochloride.

4. A method as described in claim 1, wherein the volume of isopropanol used is in the range of 2 to 20 liters per kilo of input of Thiamine hydrochloride.

5. A method as described in claim 1, wherein the mixture is agitated at a speed below 150 rpm.

6. A method as described in claim 1, wherein the mixture is agitated at a speed above 180 rpm.

7. A method as described in claim 1, wherein the crystalline Thiamine hydrochloride is Thiamine hydrochloride monohydrate in pure form.

8. A method as described in claim 1, wherein the crystalline Thiamine hydrochloride is Thiamine hydrochloride hemihydrate in pure form.

9. A method as described in claim 5, wherein the mixture is agitated at a speed below 125 rpm.

10. A method as described in claim 6, wherein the mixture is agitated at a speed above 200 rpm.

* * * * *